Figure 1:
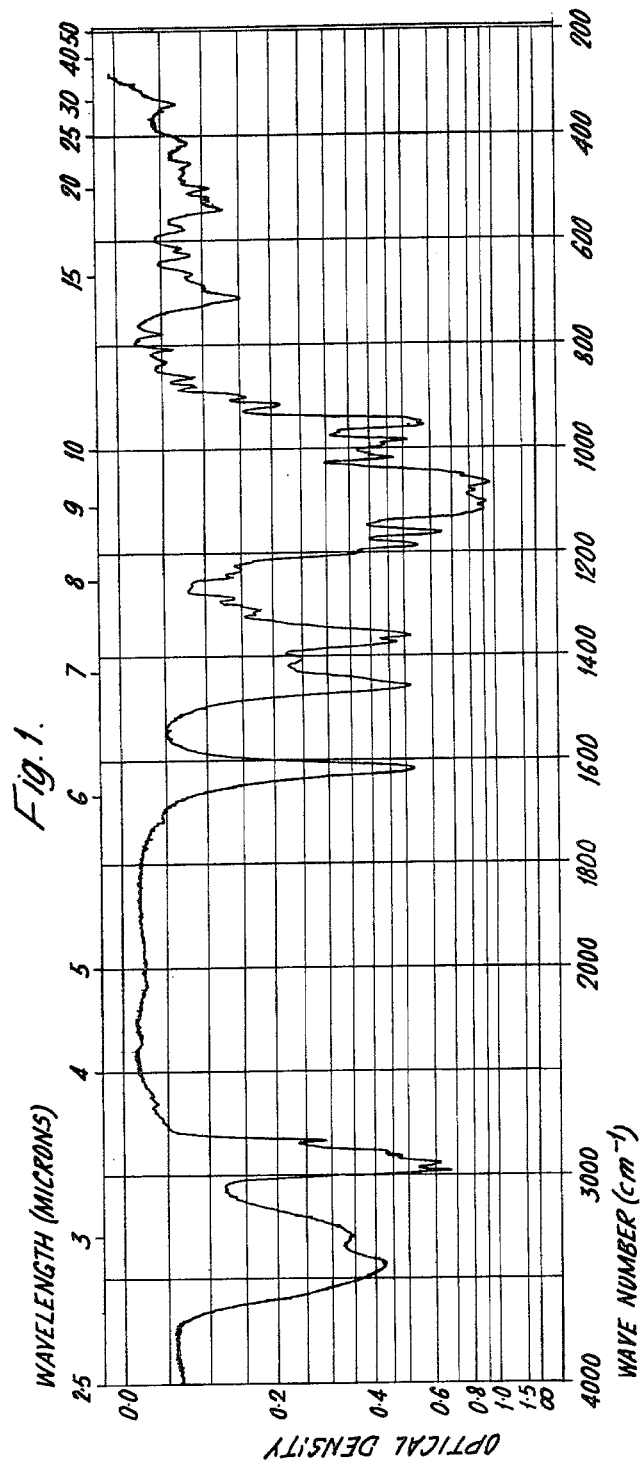

United States Patent [19]

Florent et al.

[11] 4,293,650
[45] Oct. 6, 1981

[54] ANTI-COCCIDIAL SUBSTANCE AND ITS PREPARATION

[75] Inventors: Jean Florent, Hauts de Seine; Jean Lunel, Paris; Denise Mancy, Charenton, all of France

[73] Assignee: Rhone-Poulenc Industries, France

[21] Appl. No.: 948,786

[22] Filed: Oct. 5, 1978

[30] Foreign Application Priority Data

Oct. 7, 1977 [FR] France .................. 77 30236

[51] Int. Cl.³ .................. C12P 17/18; C12N 1/20; C12R 1/465
[52] U.S. Cl. .................. 435/119; 260/345.7 R; 424/283; 435/253; 435/886
[58] Field of Search .......... 260/345.7; 424/283; 435/119, 253, 886

[56] References Cited

U.S. PATENT DOCUMENTS

| | | | |
|---|---|---|---|
| 3,907,832 | 9/1975 | Hamill | 260/345.7 |
| 3,985,872 | 10/1976 | Chamberlin | 260/345.7 |
| 3,989,723 | 11/1976 | Hamill | 260/345.7 |
| 4,132,778 | 1/1979 | Hamill et al. | 424/122 X |
| 4,133,876 | 1/1979 | Hamill et al. | 424/122 X |

*Primary Examiner*—Robert J. Warden
*Attorney, Agent, or Firm*—Stevens, Davis, Miller & Mosher

[57] ABSTRACT

37,454 RP of the formula:

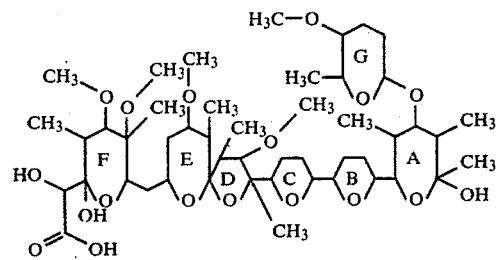

and its non-toxic salts with metals and nitrogen-containing bases possess anti-coccidial activity.

10 Claims, 3 Drawing Figures

ANTI-COCCIDIAL SUBSTANCE AND ITS PREPARATION

The present invention relates to a new antibiotic substance, hereinafter designated by the number 37,454 RP, to a process for its preparation and to compositions containing it.

The present invention provides the antibiotic 37,454 RP of the formula:

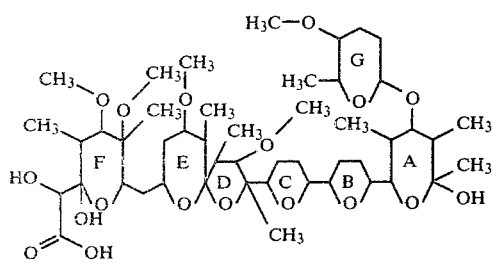

and its salts with metals and nitrogen-containing bases, which are of very particular interest by virtue of the anti-coccidial activity which they display.

37,454 RP can be obtained by cultivating a new microorganism which is identified more completely hereinafter, belongs to the genus Streptomyces and is referred to by the name *Streptomyces gypseus* DS 27,461 (NRRL 11,168).

37,454 RP is an acidic substance, the neutral equivalent weight of which is about 960 [determined with 0.1 N sodium hydroxide solution on the product in the acidic form, dissolved in a mixture of methanol and water (70:30 by volume)]. The sodium salt of 37,454 RP, the empirical formula of which is $C_{48}H_{81}O_{18}Na$, has the following physico-chemical properties:

Appearance: it is a white micro-crystalline powder.

Solubility (determined in accordance with the instructions of the French Pharmacopoeia, IXth edition, 1972): 37,454 RP (sodium salt) is virtually insoluble in water, sparingly soluble in hexane, and soluble in chlorinated solvents such as methylene chloride and chloroform, alcohols such as methanol, ketones such as acetone, esters such as ethyl acetate, and dimethyl formamide.

Percentage elementary analysis (on the compounds as obtained): 37,454 RP (sodium salt) contains carbon, hydrogen, oxygen and sodium. Its percentage composition is approximately: % Found: C 59.27% H 8.45% O 28.32% Na 2.36%. (Calculated for $C_{48}H_{81}O_{18}Na$: C 59.49% H 8.42% O 29.72% Na 2.37%).

Weight loss in vacuo: at 60° C./3 mm Hg=0.3%.

Melting point (determined in a capillary tube): 198°-199.5° C.

Optical rotation (determined on a 0.974% w/v solution in methanol). The optical rotation of 37,454 RP (sodium salt) is approximately: $[\alpha]_D^{20} = +2.3° \pm 0.6°$; $[\alpha]_{436}^{20} = +1.3° \pm 0.6°$.

Ultra-violet spectrum: 37,454 RP (sodium salt) does not exhibit a characteristic absorption.

Infra-red spectrum: (determined on tablets of a mixture with potassium bromide).

This spectrum is shown in FIG. 1 of the accompanying drawings in which the wavelengths in microns (upper scale) and the wave numbers in $cm^{-1}$ (lower scale) are plotted as abscissae and the optical densities have been plotted as the ordinate. The principal infrared absorption bands for 37,454 RP (sodium salt) are given in Table 1 below:

TABLE 1

| | | |
|---|---|---|
| 3,560 sh | 2,838 m | 1,375 m |
| 3,420 s ($H_2O$) | 2,660 vw | 1,362 s |
| 3,300 m | 2,360 vw ($CO_2$) | 1,345 sh |
| 3,260 sh | 2,080 vw | 1,335 sh |
| 3,000 sh | 1,718 vw | 1,320 sh |
| 2,980 s | 1,620 s | 1,310 m |
| 2,955 sh | 1,460 s | 1,300 sh |
| 2,940 m | 1,450 sh | 1,288 m |
| 2,915 m | 1,438 sh | 1,262 vw |
| 2,898 sh | 1,428 sh | 1,245 m |
| 2,865 sh | 1,410 sh | 1,230 m |
| 2,860 sh | 1,405 m | 1,215 sh |
| 1,200 sh | 895 sh | |
| 1,188 s | 880 w | |
| 1,162 s | 860 w | |
| 1,140 sh | 858 sh | |
| 1,130 sh | 830 vw | |
| 1,120 s | 808 w | |
| 1,105 vw | 780 w | |
| 1,098 sh | 720 sh | |
| 1,082 s | 710 m | |
| 1,070 vs | 690 sh | |
| 1,060 sh | 665 w | |
| 1,052 s | 660 sh | |
| 1,045 sh | 630 m | |
| 1,040 sh | 615 w | |
| 1,035 sh | 580 w | |
| 1,020 s | 550 w | |
| 1,010 sh | 540 m | |
| 995 m | 525 vw | |
| 985 s | 518 vw | |
| 970 sh | 500 m | |
| 955 s | 470 sh | |
| 950 m | 452 w | |
| 945 sh | 412 w | |
| 915 m | 400 sh | |
| 900 m | 340 m | | vs = very strong
m = medium
vw = very weak
s = strong
w = weak
sh = shoulder

Proton nuclear magnetic resonance spectrum in deuterated chloroform

Figure 2:
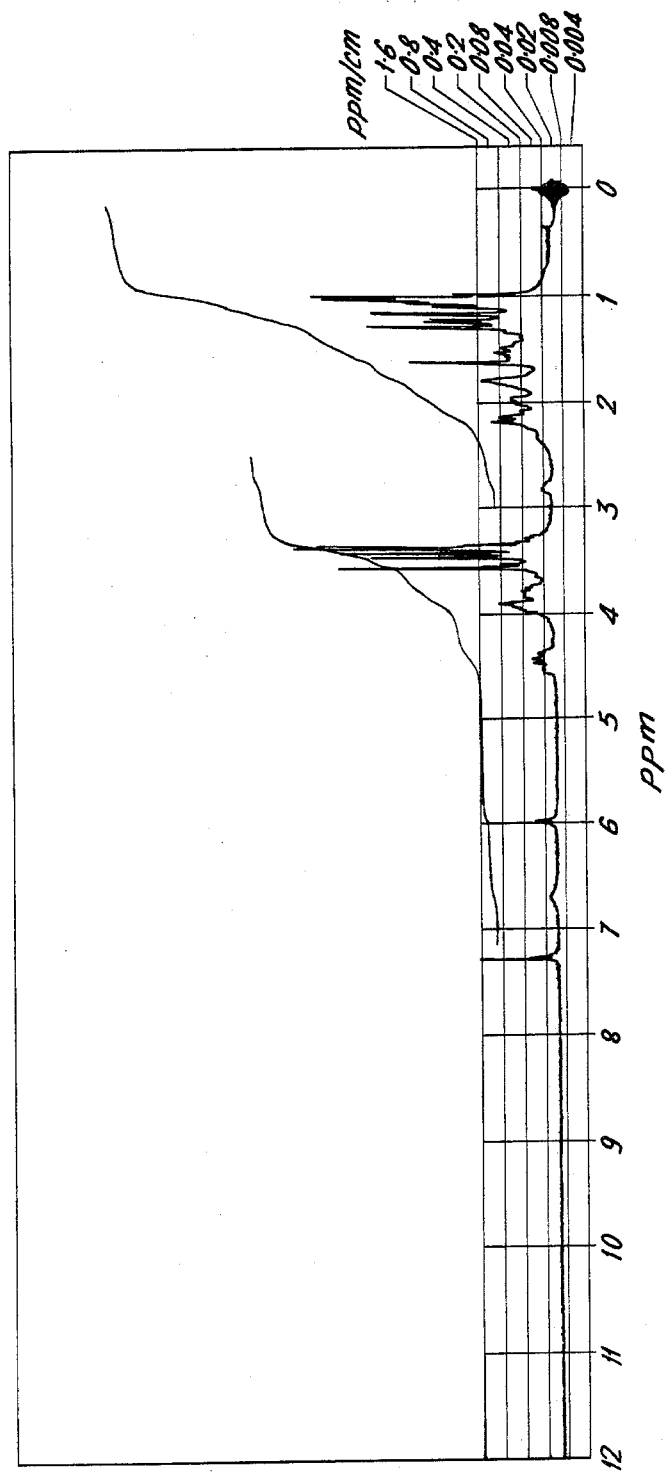

This spectrum, which is shown in FIG. 2, was recorded on a CAMECA TNS-250 spectrometer at a frequency of 250 Mc/s, on a solution, containing about 40 mg/cc, in deuterated chloroform. It exhibits the characteristics given in Table 2 below (the chemical shifts are counted positively in ppm towards the weak field, relative to TMS (tetramethylsilane) taken as an internal standard):

TABLE 2

| Chemical shift in ppm | Form of the signal; coupling constant (J) |
|---|---|
| 1.0 | doublet, J = 6.5 c/s |
| 1.03 | doublet, J = 6.5 cs |
| 1.06 | doublet, J = 6.5 c/s |
| 1.09 | doublet, J = 6.5 c/s |
| 1.17 | singlet |
| 1.24 | doublet, J = 6.5 c/s |
| 1.30 | singlet |
| 1.2 to 1.6 | multiplet |
| 1.62 | singlet |
| 1.80 | unresolved |
| 1.9 to 2.5 | multiplet |
| 2.8 | double triplet |
| 3.2 to 3.7 | multiplet |
| 3.36 | singlet |
| 3.38 | singlet |
| 3.43 | singlet |
| 3.47 | singlet |

TABLE 2-continued

| Chemical shift in ppm | Form of the signal; coupling constant (J) |
|---|---|
| 3.57 | singlet |
| 3.7 to 4.2 | multiplet |
| 4.3 to 4.6 | multiplet |
| 5.98 | broad singlet |
| 6.7 | broad singlet |

The signal with a chemical shift of about 7.3 is from chloroform (C$\underline{H}$Cl$_3$) in the deuterated chloroform solvent.

According to this spectrum, 37,454 RP (sodium salt) contains 5 methoxy groups.

$^{13}$C nuclear magnetic resonance spectrum in deuterated chloroform

Figure 3:
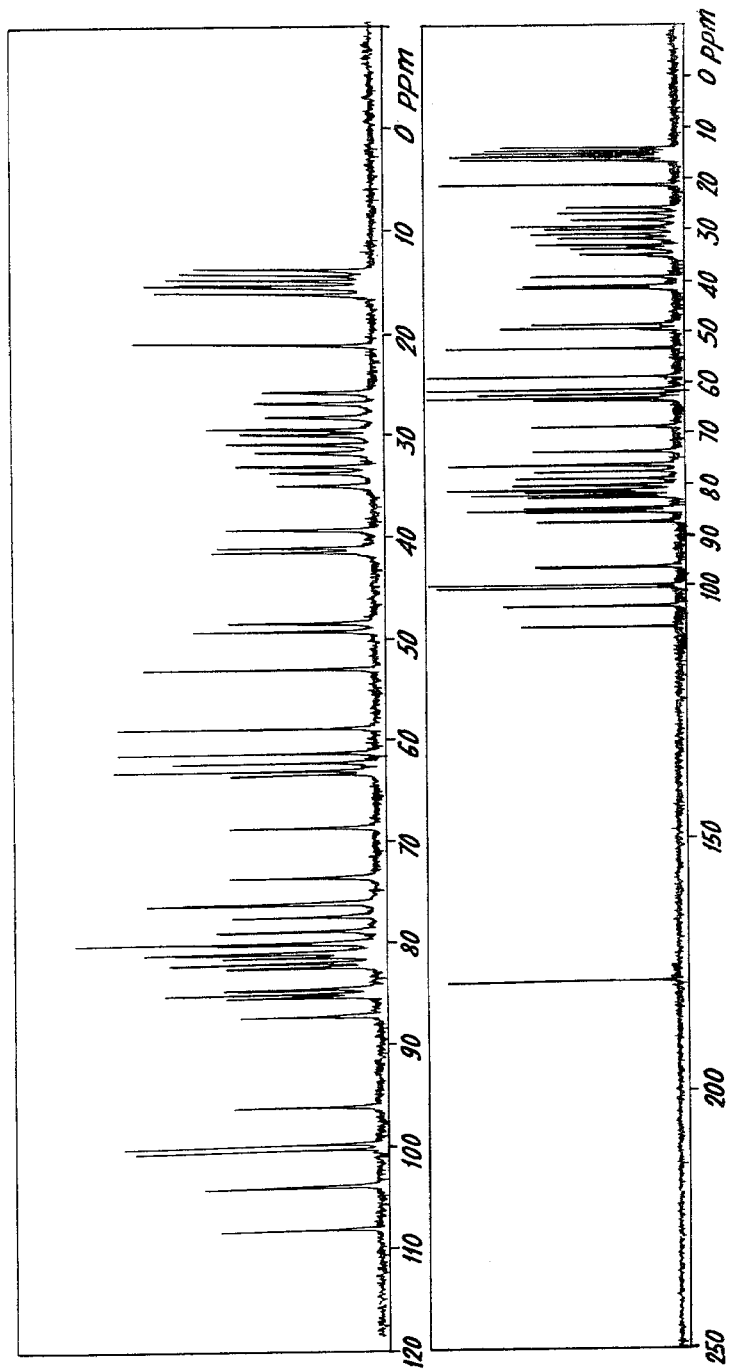

This spectrum, which is shown in FIG. 3, was recorded on a Bruker WH 90 spectrometer at a frequency of 22.63 Mc/s, on a solution, containing about 200 mg/cc, in deuterated chloroform. It exhibits the characteristics given in Table 3 below (the chemical shifts are measured positively in ppm towards the weak field, relative to deuterated chloroform taken as an internal standard at 77.0 ppm from TMS, and expressed in ppm relative to TMS taken as zero):

TABLE 3

| Chemical shifts in ppm relative to TMS | Form of the signal in the spectrum recorded in off-resonance |
|---|---|
| 11.1 | quadruplet |
| 11.7 | quadruplet |
| 12.3 | quadruplet |
| 12.7 and 12.7 | quadruplet |
| 13.6 | quadruplet |
| 18.4 | quadruplet |
| 27.0 | quadruplet |
| 28.5 | quadruplet |
| 23.2 | triplet |
| 24.3 | triplet |
| 25.7 and 25.7 | triplet |
| 29.2 | triplet |
| 30.6 | triplet |
| 31.2 | triplet |
| 32.5 | triplet |
| 36.9 | doublet |
| 38.7 | doublet |
| 39.1 | doublet |
| 46.2 | doublet |
| 47.0 | doublet |
| 50.8 | quadruplet |
| 56.7 | quadruplet |
| 59.2 | quadruplet |
| 60.2 | quadruplet |
| 60.9 | quadruplet |
| 61.3 | doublet |
| 66.7 | doublet |
| 71.8 | doublet |
| 74.3 and 74.3 | doublet |
| 79.3 and 79.3 | doublet |
| 79.7 | doublet |
| 80.3 | doublet |
| 80.7 | doublet |
| 82.8 | doublet |
| 83.6 | doublet |
| 85.5 | doublet |
| 78.5 | singlet |
| 83.3 | singlet |
| 94.5 | doublet |
| 98.2 | singlet |
| 98.2 | singlet |
| 102.5 | doublet |
| 106.8 | singlet |
| 178.4 | singlet |

According to this spectrum, 37,454 RP (sodium salt) contains 48 carbon atoms.

Mass spectrum: the field desorption mass spectrum shows, for the sodium salt, a molecular peak corresponding to a mass of 968 (theoretical value: 968).

Chromatographic migration: 37,454 RP (sodium salt) can be characterised by ascending thin layer chromatography on silica gel: using as eluent a mixture of methylene chloride and methanol (94:6 by volume), the Rf is 0.75.

Bacteriostatic activity in vitro: the bacteriostatic activity of 37,454 RP (sodium salt) was determined in relation to a certain number of microorganisms, by one of the dilution methods usually employed for this purpose. For each microorganism, the lowest concentration of active substance which, under defined conditions, prevents any visible development in a suitable nutrient broth was determined. The results of the various determinations are summarised in Table 4 below, where the minimum bacteriostatic concentrations are expressed in micrograms of substance per cc of test medium:

TABLE 4

| Bacterial organism tested | Minimum bacteriostatic concentrations in μg/cc) |
|---|---|
| Staphylococcus aureus, strain 209 P-ATCC 6538 P | 0.6 |
| Staphylococcus aureus, Smith strain | 0.8 |
| Sarcina lutea - ATCC 9341 | 0.9 |
| Streptococcus faecalis - ATCC 8043 | 0.3 |
| Streptococcus pyogenes haemolyticus, Dig 7 strain (Institut Pasteur) | 0.6 |
| Diplococcus pneumoniae, Til strain (Institut Pasteur) | 0.1 |
| Neisseria catarrhalis (A 152, Institut Pasteur) | >20 |
| Bacillus subtilis - ATCC 6633 | 0.8 |
| Bacillus cereus - ATCC 6630 | 0.3 |
| Mycobacterium species - ATCC 607 | 10 |
| Escherichia coli - ATCC 9637 | >50 |
| Shigella dysenteriae, Shiga L (Institut Pasteur) | >50 |
| Salmonella schottmuelleri (paratyphi B), Fougenc strain (Institut Pasteur) | >50 |
| Proteus vulgaris | >50 |
| Pseudomonas aeruginosa | >15 |

Acute toxicity: in mice, the 50% lethal dose (LD$_{50}$) is 90 mg/kg given orally in a single dose.

Anti-coccidial activity: the anti-coccidial activity was determined in chickens infested in particular with *Eimeria tenella* and *Eimeria acervulina*.

The anti-coccidial activity of 37,454 RP (sodium salt), incorporated into chicken feed, manifests itself at non-toxic concentrations of between 0.005% and 0.04% by weight of the sodium salt in the feed.

The organism which produces antibiotic 37,454 RP is a strain of Streptomyces which was isolated from a sample of soil taken in Algeria, and to which the number DS 27,461 has been given. A sample of this organism was deposited with the Northern Regional Research Laboratory of the Agriculture Research Service (ARS) of the U.S. Department of Agriculture at Peoria, Ill. (U.S.A.) on July 29th 1977 and has been recorded under the reference number NRRL 11,168. A sample of *S. gypseus* (NRRL 11,168) can be obtained from that laboratory by any person who refers to the present publication.

This organism, which exhibits characteristics which have not allowed it to be identified with any previously described species, must be considered as a new species and has been given the name *Streptomyces gypseus* DS 27,461.

It was isolated by following the general method which consists of suspending a small amount of soil in sterile distilled water, diluting the suspension to various concentrations and spreading a small volume of each dilution on the surface of Petri dishes containing a nutrient agar medium. After an incubation period of several days at 26° C., which allows the microorganisms to develop, the colonies which it is desired to isolate in order to investigate them further are taken and transplanted onto nutrient agars in order to obtain more abundant cultures. *Streptomyces gypseus* DS 27,461 forms oval spores, measuring 0.9 to 1.2 $\mu$/0.5 to 0.8$\mu$, of which the wall, observed under the electron microscope, appears smooth. Its chains of spores in general comprise 10 to 20 spores; these usually coil up to form more or less open spirals of 1 to 3 or 4 turns, and are most commonly grouped along a filament, forming more or less elongated clusters. According to its mode of sporulation, this strain is to be classified under the Spira section of the Pridham classification.

*Streptomyces gypseus* DS 27,461 develops well at 26° C. and at 37° C., but not at 50° C. It exhibits a sporulated aerial mycelium of white colour. Its vegetative mycelium is in general coloured greyish to brownish grey or pale yellowish brown; sometimes, however, on certain media such as glycerol-asparagine agar or glucose-peptone agar, certain zones are prone to assume a reddish or violet colour. On the majority of agar media on which it is cultured, it forms soluble pigments, the colour of which is brownish to brown-grey or pale yellow-brown, and sometimes pinkish brown.

In its cultures carried out at 26° C., it exhibits the following biochemical characteristics:

TABLE 5

| | |
|---|---|
| Production of melanin | negative |
| Production of $H_2S$ | negative |
| Tyrosinase | negative |
| Liquefaction of gelatin | positive |
| Utilisation of cellulose | negative |
| Production of nitrites from nitrates | negative on nitrate-containing nutrient broth; positive on synthetic broths |
| Hydrolysis of starch | positive |
| Culture of skimmed milk | no coagulation or peptonisation; pH unchanged in 1 month |

Its capacity to use various sources of carbon to ensure its development was determined in accordance with the principle of the method of Pridham and Gottlieb (J. of Bact. 56, 107-114, 1948). The results are indicated in Table 6 below:

TABLE 6

| Sources of carbon tested | Utilisation |
|---|---|
| D-Glucose | positive |
| D-Xylose | positive |
| L-Arabinose | positive |
| L-Rhamnose | positive |
| D-Fructose | positive |
| D-Galactose | positive |
| Raffinose | positive |
| D-Mannitol | positive |
| Inositol | positive |

TABLE 6-continued

| Sources of carbon tested | Utilisation |
|---|---|
| Salicin | negative |
| Sucrose | positive |

The culture characteristics of *Streptomyces gypseus* DS 27,461 are summarised in Table 7 below. They are those of cultures which have reached a good stage of development, that is to say of about 2 to 3 weeks at 26° C., unless otherwise indicated. These characteristics were observed on nutrient agars, and on broths, usually employed for determining the morphological characteristics of strains of Streptomyces, the cultures on agar media being carried out on agar slopes. A certain number of culture media employed were prepared in accordance with the formulations given in "The Actinomycetes", S. A. WAKSMAN, p. 193-197, Chronica Botanica Company, Waltham, Mass., U.S.A., 1950; in this case, they are indicated by the letter W followed by the number which they have been given in "The Actinomycetes". The references or compositions of the other media are as follows:

Ref. A. "Hickey and Tresner's Agar"—T. G. PRIDHAM et al.—Antibiotics Annual, 1956-1957, p. 950.

Ref. B. "Bennett's Agar"—S. A. WAKSMAN—The Actinomycetes, vol. 2, p. 331, No. 30—The Williams and Wilkins Company, Baltimore, 1961.

Ref. C. "Emerson's agar" (Formula W-23 with addition of 2% of agar).

Ref. D. "Yeast Extract Agar"—T. G. PRIDHAM et al.—Antibiotics Annual, 1956-1957, p. 950.

Ref. E. "Tomato Paste Oatmeal Agar"—T. G. PRIDHAM et al.—Antibiotics Annual, 1956-1957, p. 950.

Ref. F. "Melanin Formation Medium" (Tyrosine-yeast extract agar for melanin formation)—S. A. WAKSMAN—The Actinomycetes, vol. 2, p. 333—No. 42—The Williams and Wilkins Company, Baltimore, 1961.

Ref. G. Krainsky's calcium malate agar. W. E. GRUNDY et al.—Antibiotics and Chem. 2, 401, 1952.

Ref. H. "Inorganic Salts—Starch Agar"—T. G. PRIDHAM et al.—Antibiotics Annual, 1956-1957, p. 951.

Ref. I. Corresponds to formula W-1, with 3% of sucrose replaced by 1.5% of glucose.

Ref. J. Corresponds to formula W-1, with 3% of sucrose replaced by 1.5% of glycerol.

Ref. K. Corresponds to formula W-18, with 3% of sucrose replaced by 1.5% of glucose.

Ref. L. Corresponds to formula W-18, with the sucrose omitted and replaced by small strips of filter paper partially immersed in the liquid.

Ref. M. Bacto Nitrate Broth (Difco).

Ref. N. "Plain gelatin"—pure 12% strength gelatin prepared in accordance with the instructions in "Manual of Methods for Pure Culture Study of Bacteria"—Society of American Bacteriologists, Geneva, N.Y.—$II_{50}$-18.

Ref. P. Commercial skimmed milk powder, reconstituted in accordance with the manufacturer's instructions.

Ref. Q. Medium described for research on the production of $H_2S$ by: H. D. TRESNER and F. DANGA—Journal of Bacteriology, 76, 239-244, 1958.

The culture media are referred to in Table 7, which follows, by their reference letters. The media indicated by the letter W are as follows:
W-7: glucose-peptone agar.
W-5: nutrient agar.
W-12: ovalbumin agar.
W-2: glucose-asparagine agar.
W-3: glycerol-asparagine agar.
W-10: starch-nitrate agar.
W-1: Czapek synthetic agar containing sucrose.
W-19: starch-nitrate broth.
W-27: culture on potato.
W-28: culture on carrot.

TABLE 7

| Culture medium | Degree of development | Vegetative mycelium (V.m. or underside of the culture) | Aerial structure (comprising the combination of the aerial mycelium and the sporulation) | Soluble pigment | Observations and biochemical properties |
|---|---|---|---|---|---|
| Ref. A | Fairly good | V.m. brownish grey | White. Very moderately developed | Pinkish brown | Oval spores measuring 0.9 to 1.2 $\mu$/0.5 to 0.8 $\mu$. Chains of spores coiling up into spirals of 1 to 3 or 4 turns. Sporophores in clusters. |
| Ref. B | Good | V.m. pale brownish | White. Moderately developed | Rather pale yellow-brown | |
| Ref. C | Good | V.m. greyish yellow brown | Whitish. Very moderately developed | Rather pale orange-brown | |
| Ref. D | Very good | V.m. brown-grey | White. Moderately developed | Rather pale yellow-brown | |
| Ref. E | Good | V.m. grown-grey to violet-brown | White. Very moderately developed | Rather pale brownish | |
| W-7 | Fairly good | V.m. brownish grey assuming a reddish violet colour in places | White. Very moderately developed | Pinkish brown-grey | |
| W-5 | Moderate | Underside yellow-brown | White. Very moderately developed | Pale yellow-brown | |
| Ref. F | Moderate | Underside brownish yellow | White. Moderately developed | None | Production of melanin negative (readings) taken in accordance with the recommendations of the author) |
| Ref. G | Fairly good | Underside greyish brown | White. Moderately developed | Pale greyish | No solubilisation of calcium malate |
| W-12 | Very poor | V.m. colourless to greyish | None | None | |
| W-2 | Poor | V.m. colourless to greyish. Underside light yellowish | None | None | |
| W-3 | Moderate | V.m. brownish yellow-grey with some reddish violet zones | Whitish. In the form of traces | Very pale brownish | |
| Ref. H | Fairly good | V.m. brownish | White Moderately developed | Pale brownish grey | Oval spores measuring 0.9 to 1.2 $\mu$/0.5 to 0.8 $\mu$. Chains of spores coiling up into spirals of 1 to 3 or 4 turns. Hydrolysis of starch: positive |
| W-10 | Moderate | Underside yellow-brown | Whitish. Very moderately developed | Pale yellowish brown | Hydrolysis of starch: positive |
| W-1 | Fairly good | Underside-yellow brown | White. Rather well developed | Brown-grey | |
| Ref. I | Fairly good | V.m. brownish grey. Underside yellow-brown | White. Rather well developed | Brown-grey | |
| Ref. J | Fairly good | V.m. yellowish brown. Underside yellow-brown | Whitish. In the form of traces | Pale yellow-brown | |
| W-19 | Fairly | Rather well-formed | Whitish. In the | None | Formation of |

TABLE 7-continued

| Culture medium | Degree of development | Vegetative mycelium (V.m. or underside of the culture) | Aerial structure (comprising the combination of the aerial mycelium and the sporulation) | Soluble pigment | Observations and biochemical properties |
| --- | --- | --- | --- | --- | --- |
| | good | velum. V.m. yellowish white | form of traces | | nitrites: positive |
| Ref. K | Very moderate | Culture whitish, on the surface | None | None | Formation of nitrites: positive |
| Ref. L | None | | | None | No utilisation of the cellulose |
| Ref. M | Fairly good | Rather well-formed ring. Underside light yellowish | White. Moderately developed | None | Formation of nitrites: negative (checks made after 24 hours, 48 hours, 7 days, 15 days and 28 days of incubation at 26° C.) |
| Ref. N | Good | V.m. greyish white | White. In the form of traces | Light yellow | Liquefaction gelatin: good |
| W-27 | Good | V.m. very thick and very wrinkled, pale brownish | White. Very moderately developed | Pale brownish grey | |
| W-28 | Very poor | V.m. greyish. Very poorly developed | None | None | |
| Ref. P | Moderate | Cream to pink-brown ring | None | None | No coagulation. No peptonisation. pH unchanged in 1 month |
| Ref. Q | Fairly good | V.m. brownish grey | Whitish. In the form of traces | Yellow-brown | Production of H$_2$S: negative. (readings taken according to the recommendations of the authors) |

The combination of characteristics exhibited by Streptomyces gypseus DS 27,461 does not coincide exactly with any of those which are exhibited by the species described in the usual reference manuals (Bergey's Manual of Determinative Bacteriology, 7th edition, 1957, and 8th edition, 1974, as well as "The Actinomycetes", S. A. Waksman, The Williams and Wilkins Company, 1961); for this reason it must be considered a new species. In fact, S. gypseus DS 27,461 exhibits a sporulated aerial mycelium of white colour, does not give melanin pigments on organic media, and forms chains of spores which coil up into spirals, the walls of the spores observed under the electron microscope appearing smooth. The species to which it comes closest amongst those which have been described is Streptomyces albus which also exhibits the four characteristics which have just been mentioned and furthermore forms a vegetative mycelium which can range from colourless to cream-coloured or brownish and, when it forms a soluble pigment, colours its culture medium brownish. However, contrary to S. albus, which in general does not give a soluble pigment on any of its culture media or only occasionally gives a brownish soluble pigment, S. gypseus DS 27,461 produces much more commonly soluble pigments of brownish to brown-grey or pale yellow-brown, and sometimes pinkish brown, colour in its agar culture media. Furthermore, S. gypseus DS 27,461 contrary to S. albus, forms, on certain agar media, in particular glucose-peptone agar and glycerol-asparagine agar, and also when cultured on skimmed milk, a vegetative mycelium which tends to colour partially in a reddish pink to purplish blue or violet colour. It should also be noted that S. gypseus DS 27,461 forms a light yellow soluble pigment on gelatin, neither peptonises nor coagulates skimmed milk, and does not change the pH of skimmed milk significantly in 1 month, and only exhibits extremely poor development on carrot, whilst S. albus does not form a soluble pigment on gelatin, coagulates skimmed milk and peptonises it rapidly, rendering it alkaline, and exhibits excellent development on carrot. Finally, S. gypseus DS 27,461 utilises L-arabinose, L-rhamnose, raffinose and inositol and does not utilise salicin, whilst S. albus does not utilise L-arabinose, L-rhamnose, raffinose and inositol, and utilises salicin.

According to the invention 37,454 RP or a salt thereof with a metal or a nitrogen-containing base is prepared by cultivating Streptomyces gypseus DS 27,461, or a productive mutant thereof (i.e. a mutant capable of producing 37,454 RP), aerobically in a culture medium containing assimilable sources of carbon, nitrogen and inorganic substances, and isolating the 37,454 RP formed during the culture as such or as a salt thereof.

The culture of Streptomyces gypseus DS 27,461 can be carried out by any method of aerobic surface culture or submerged culture but the latter is to be preferred for reasons of convenience. For this purpose, the various types of apparatus which are usually employed in the fermentation industry are utilised.

In particular, the following procedure can be adopted for carrying out the culture:

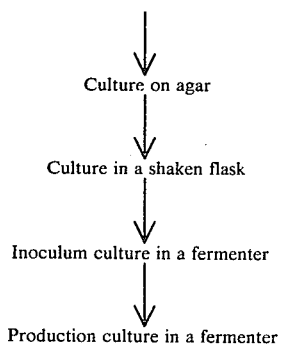

Streptomyces gypseus DS 27,461-Stock
↓
Culture on agar
↓
Culture in a shaken flask
↓
Inoculum culture in a fermenter
↓
Production culture in a fermenter The culture medium must essentially contain a source of assimilable carbon and a source of assimilable nitrogen, mineral components and, if appropriate, growth factors. These constituents can be introduced as well-defined products or as complex mixtures, such as are encountered in biological products of various origins.

As sources of assimilable carbon, it is possible to use carbohydrates such as glucose or sucrose, or other carbon-containing substances such as sugar alcohols (e.g. mannitol). Certain animal oils or vegetable oils such as lard oil or soya oil can advantageously replace these various sources of carbon, or can be added to them.

The suitable sources of assimilable nitrogen are extremely varied. They can be very simple chemical substances such as inorganic or organic ammonium salts, urea and certain aminoacids. Nitrogen can also be introduced through complex substances which principally contain the nitrogen in the form of a protein, for example casein, lactalbumin, gluten and their hydrolysis products, soya flour, groundnut flour, fishmeal, meat extract, yeast extract, distillers solubles and corn steep liquor.

Amongst the mineral components which may be added, some may have a buffering or neutralising effect, such as the alkali metal phosphates or alkaline earth metal phosphates or calcium carbonate or magnesium carbonate. Others provide the ionic equilibrium required for the development of *Streptomyces gypseus* DS 27, 461 and for the production of 37,454 RP, such as the chlorides and sulphates of alkali metals and alkaline earth metals. Finally, some of them act more especially as activators of the metabolic reactions of *Streptomyces gypseus* DS 27.461; e.g. the salts of zinc, cobalt, iron, copper and manganese.

The growth factors are products of a vitamin nature, such as riboflavin, folic acid and pantothenic acid.

The pH of the culture medium at the start of the culture should be between 6.2 and 7.8 and preferably between 6.6 and 7.4. The optimum temperature for the culture is between 25° and 30° C., but satisfactory production is achieved at temperatures of between 23° and 33° C. Aeration of the culture medium can vary between rather wide values. However, it has been found that aerations of 0.3 to 3 liters of air per liter of broth per minute are particularly suitable. The maximum yield of 37,454 RP is achieved after 4 to 8 days' culture; this time depends essentially on the medium used.

It can be seen from the preceding text that the general conditions of culture of *Streptomyces gypseus* DS 27,461 in order to produce 37,454 RP can vary widely and can be adapted to particular requirements.

37,454 RP can be isolated from the fermentation broths as follows:

The broth is filtered at an acid pH, generally between 2 and 5 and preferably about 3, in the presence of a filtration aid. The activity retained in the filter cake is extracted by means of a suitable organic solvent, e.g. a lower alcohol such as methanol or a chlorinated solvent such as methylene chloride. The crude product can be isolated from the extract by crystallisation after concentration under reduced pressure, if appropriate adding a poor solvent or a non-solvent for 37,454 RP, and cooling the solution.

37,454 RP can be purified, depending on whether it is in the form of the acid or of a salt, by the conventional methods used, such as recrystallisation or chromatography on various adsorbents or by countercurrent distribution. The conversion of the acid 37,454 RP to one of its salts, or vice versa, and the conversion of a salt to another salt, are carried out by applying conventional methods.

Examples of salts which can be used are the sodium and potassium salts.

The present invention also includes within its scope a culture of the microorganism *Streptomyces gypseus* DS 27,461 (NRRL 11,168) in a synthetic culture medium containing a source of assimilable carbon, a source of assimilable nitrogen and inorganic substances, and substantially free from other microorganisms.

The invention is illustrated by the following Example.

EXAMPLE 1

(a) Fermentation

The following are introduced into a 170 liter fermenter:

| | |
|---|---|
| peptone | 1,200 g |
| yeast extract | 600 g |
| glucose monohydrate | 1,200 g |
| agar | 240 g |
| water, q.s.p. | 110 liters. |

The pH of the medium is adjusted to 7.0 by adding 10 N sodium hydroxide solution (25 cc). The medium is sterilised by bubbling steam at 122° C. through it for 40 minutes. After cooling, the volume of the broth is 120 liters due to the condensation of steam during sterilisation; the pH at this stage is 6.85. The medium is inoculated with a culture (200 cc) of *Streptomyces gypseus* DS 27,461 produced in a shaken Erlenmeyer flask. The culture is developed at 30° C. for 27 hours, whilst shaking and aerating with sterile air; it is then suitable for the inoculation of the production culture.

The production culture is carried out in an 800 liter fermenter charged with the following substances:

| | |
|---|---|
| corn steep liquor (50% solids content) | 8 kg |
| glucose monohydrate | 12 kg |
| ammonium sulphate | 0.8 kg |
| water q.s.p. | 370 liters. |

The pH is adjusted to 7.20 by adding 10 N sodium hydroxide solution (910 cc). Thereafter, the following is added:

calcium carbonate: 3 kg.

At this stage the pH of the medium is 7.30. The medium is sterilised by bubbling steam at 122° C. through it for 40 minutes. After cooling, the volume of the medium is 400 liters due to the condensation of steam during sterilisation; the pH is 7.10. The medium is then inoculated with inoculum culture (40 liters) from the 170 liter fermenter, described above.

The culture is developed for 116 hours at 27° C., with agitation using a stirrer rotating at 205 rpm and aeration with sterile air (20 cubic meters/hour); the pH of the culture at this stage is 7.90, and the volume of the broth is 400 liters. The antibiotic activity of the broth, determined by a dilution method using staphylococci, is 860 u/cc.

(b) Extraction

The broth (400 liters) obtained as indicated above is brought to a pH of 3 by adding 6 N sulphuric acid (6 liters) and is stirred for half an hour. After adding a filtration aid (20 kg), the broth is filtered on a filter press and the filter cake is washed on the filter with water (100 liters), the pH of which is brought to 3 by adding 6 N sulphuric acid. The filtrate and the wash liquor are discarded. The filtration cake is dispersed in methanol (230 liters); the pH of the mixture is adjusted to 7.8 by adding 6 N sodium hydroxide solution (1.15 liters) and the mixture then stirred for half an hour. The mixture is filtered on a filter press and the filter cake is washed on the filter with a methanol-water mixture (75:25 by volume; 100 liters). The filtrate and the wash liquor are combined and concentrated under reduced pressure (5 to 10 mm Hg) to give an aqueous concentrate (15 liters). The concentrate obtained gives a precipitate after standing for 15 hours at +4° C.

The precipitate is drained by centrifuging and then dried at 30° C. under reduced pressure (1 to 5 mm Hg) for 15 hours. The crude sodium salt of 37,454 RP (90 g) is thus isolated.

(c) Purification

The crude product obtained above is dissolved in methylene chloride (2 liters). The solution is stirred for 1 hour. An insoluble material is removed by centrifuging. The supernatant liquor is concentrated by distillation under reduced pressure (5 to 10 mm Hg) until its volume is 200 cc and is then poured into n-hexane (10 liters). The precipitate obtained is removed by centrifuging. The supernatant liquor is concentrated under reduced pressure (5 to 10 mm Hg) until its volume is 800 cc and is then left to stand. After standing for 48 hours at +4° C., the crystals formed are filtered off, washed with hexane (100 cc) at −10° C. and dried under reduced pressure at 35° C. (5 mm Hg). Crystalline 37,454 RP in the form of its sodium salt (61 g) is thus isolated.

(d) Recrystallisation

The crystals obtained above are dissolved in acetone (1.2 liters) and the solution is stirred for 30 minutes. An insoluble material is removed by centrifuging. Decolourising charcoal (5 g) which has been washed with hydrochloric acid is added, the mixture is again stirred for half an hour and finally the decolourising charcoal is removed by filtration. Distilled water (600 cc) is added to the gently stirred filtrate. The sodium salt of 37,454 RP crystallises slowly at +4° C. The crystals are isolated by filtration, washed with a mixture of acetone and water (50:50 by volume; 200 cc) and dried under reduced pressure at 35° C. The sodium salt of pure 37,454 RP (42 g) is thus obtained.

The present invention includes within its scope anti-coccidial compositions for feeding to animals which contain 0.005% to 99.9% by weight of 37,454 RP or a non-toxic salt thereof with a metal or a nitrogen-containing base and a substance capable of being consumed by animals. Such compositions include mixed animal feeds, or concentrated mixtures for animal nutrition, which contain 37,454 RP or a non-toxic salt thereof with a metal or a nitrogen-containing base, and optionally another anti-coccidial agent. By the term "non-toxic salt" as used in this specification is meant a salt the cation of which is innocuous to the animal organism at the dosage used.

The dose required to produce a suitable effect can of course vary within fairly wide limits depending on the nature of the feedstuffs themselves.

In general terms, it suffices if the feedstuffs provided for the animals contain from 0.005 to 0.04% by weight of 37,454 RP or a non-toxic salt thereof with a metal or a nitrogen-containing base.

37,454 RP or its non-toxic salts with metals or nitrogen-containing bases can be uniformly distributed in the complete composite feedstuffs at the above doses. They can also be distributed in supplementary feedstuffs, most frequently together with the other additives such as vitamins and mineral salts. These supplementary feedstuffs can either be mixed with the rations or consumed as such; they usually represent 5 to 20% of the rations.

The premixes used for the preparation of the complete rations or supplementary feedstuffs usually contain from 0.05 to 20% by weight of 37,454 RP or a non-toxic salt thereof with a metal or a nitrogen-containing base, diluted with an edible extender. They constitute a convenient intermediate which facilitates the uniform distribution of the active product in the feedstuffs. The premixes themselves are generally obtained from concentrates which contain from 99.9 to 20% of 37,454 RP or a non-toxic salt thereof with a metal or a nitrogen-containing base, to which have been added edible denaturing agents such as edible dyestuffs, flavourings, dispersing agents or anti-agglomeration agents, and edible extenders.

The concentrates and premixes are generally powders. The supplementary feedstuffs and the complete composite feedstuffs can be either powders or in the form of granules prepared in accordance with the usual techniques.

The following Example illustrates compositions according to the invention.

EXAMPLE 2

A basic feedstuff having the following composition is prepared:

| | |
|---|---|
| Cereal middlings | 13.41% |
| Barley flour | 13.41% |
| Maize flour | 13.41% |
| Wheat flour | 31.32% |
| Fishmeal | 8.92% |
| Soya flour | 8.92% |
| Dehydrated fodder flour | 4.56% |
| Yeast extract | 2.33% |
| Dried milk powder | 2.68% |
| Sodium chloride | 0.09% |
| Calcium chloride | 0.89% |
| Mineral components | 0.06% |
| Vitamin complex: | |
| Vitamin A | 4,000 I.U./kg |
| Vitamin $D_3$ | 1,000 I.U./kg |
| Choline chloride | 11.5 mg/kg |
| Riboflavin | 2.24 mg/kg |

0.02% of 37,454 RP is added to and distributed uniformly throughout this feedstuff.

We claim:

1. A process for the preparation of the anticoccidial substance hereinbefore designated 37,454 RP of the formula:

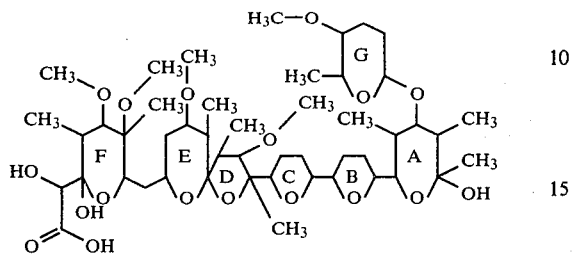

which, in the form of its sodium salt, has the following properties:

it is a white crystalline powder which is soluble in methylene chloride and chloroform, methanol, dimethyl formamide, acetone and ethyl acetate, sparingly soluble in hexane and virtually insoluble in water;

it has the following approximate elementary composition; C% 59.27, H% 8.45, O% 28.32 and Na% 2.36; which is compatible with the empirical formula $C_{48}H_{81}O_{18}Na$;

its melting point (determined in a capillary tube) is 198°–199.5° C.;

its optical rotation (determined in methanolic solution at a concentration of 0.974%) is approximately: $[\alpha]_D^{20} = +2.3 \pm 0.6°$; $[\alpha]_{436}^{20} = +1.3 \pm 0.6°$;

it does not exhibit a characteristic absorption in its ultraviolet spectrum;

it exhibits the following characteristic absorption bands in its infra-red spectrum (determined on tablets of a mixture with potassium bromide): 3,560 (shoulder), 3,420 (strong) ($H_2O$), 3,300 (medium), 3,260 (shoulder), 3,000 (shoulder), 2,980 (strong), 2,955 (shoulder), 2,940 (medium), 2,915 (medium), 2,898 (shoulder), 2,865 (shoulder), 2,860 (shoulder), 2,838 (medium), 2,660 (very weak), 2,360 (very weak) ($CO_2$), 2,080 (very weak), 1,718 (very weak), 1,620 (strong), 1,460 (strong), 1,450 (shoulder), 1,438 (shoulder), 1,428 (shoulder), 1,410 (shoulder), 1,405 (medium), 1,375 (medium), 1,362 (strong), 1,345 (shoulder), 1,335 (shoulder), 1,320 (shoulder), 1,310 (medium), 1,300 (shoulder), 1,288 (medium), 1,262 (very weak), 1,245 (medium), 1,230 (medium), 1,215 (shoulder), 1,200 (shoulder), 1,188 (strong), 1,162 (strong), 1,140 (shoulder), 1,130 (shoulder), 1,120 (strong), 1,105 (very strong), 1,098 (shoulder), 1,082 (strong), 1,070 (very strong), 1,060 (shoulder), 1,052 (strong), 1,045 (shoulder), 1,040 (shoulder), 1,035 (shoulder), 1,020 (strong), 1,010 (shoulder), 995 (medium), 985 (strong), 970 (shoulder), 955 (strong), 950 (medium), 945 (shoulder), 915 (medium), 900 (medium), 895 (shoulder), 880 (weak), 860 (weak), 858 (shoulder), 830 (very weak), 808 (weak), 780 (weak), 720 (shoulder), 710 (medium), 690 (shoulder), 665 (weak), 660 (shoulder), 630 (medium), 615 (weak), 580 (weak), 550 (shoulder), 540 (medium), 525 (very weak), 518 (very weak), 500 (medium), 470 (shoulder), 452 (weak), 412 (weak), 400 (shoulder), and 340 (medium) $cm^{-1}$;

it has a proton nuclear magnetic resonance spectrum which shows that it contains 5 methoxy groups;

it has a $^{13}C$ nuclear magnetic resonance spectrum which shows that it contains 48 carbon atoms;

it has a field desorption mass spectrum which shows a molecular peak corresponding to a mass of 968; and it has an Rf of 0.75 in ascending thin layer chromatography on silica gel, using as eluent a mixture of methylene chloride and methanol (94:6 by volume); or a non-toxic salt of 37,454 RP with a metal or a nitrogen-containing base which process comprises cultivating *Streptomyces gypseus* DS 27,461 (NRRL 11,168) or a productive mutant thereof, aerobically in a culture medium containing assimilable sources of carbon, nitrogen, and inorganic substances, and isolating the 37,354 RP formed during the culture as such or as a non-toxic salt thereof.

2. A process according to claim 1 in which the culture is carried out under submerged aerobic conditions at a temperature between 23° and 33° C. and commencing a pH between 6.2 and 7.8.

3. A process according to claim 1 in which the pH of the culture medium at the beginning of the culture is between 6.6 and 7.4.

4. A process according to claim 1 in which the culture is carried out at between 25° and 30° C.

5. A process according to claim 1 in which the culture medium is aerated at a rate of 0.3 to 3 liters of air per liter of broth per minute.

6. A process according to claim 1 in which the culture is carried out for 4 to 8 days.

7. A process according to claim 1 in which 37,454 RP is isolated from the culture medium by filtering the culture medium at an acid pH in the presence of a filtration aid, extracting 37,454 RP from the filter cake by means of a lower alcohol or a chlorinated solvent and isolating the 37,454 RP from the extract by crystallisation after concentration under reduced pressure, if necessary adding a poor solvent or a non-solvent for 37,454 RP and cooling the solution.

8. A process according to claim 7 in which the culture medium is filtered at a pH between 2 and 5 and the lower alcohol is methanol or the chlorinated solvent is methylene chloride.

9. A process according to claim 1 in which the 37,454 RP is isolated as its sodium salt.

10. A biologically pure culture of the microorganism *Streptomyces gypseus* DS 27,461 having the identifying characteristics of NRRL 11,168, said culture being capable of producing the antibiotic 37,454 RP in a recoverable quantity upon fermentation in an aqueous nutrient medium containing assimilable sources of carbon, nitrogen and inorganic substances.

* * * * *